United States Patent [19]

Eckels

[11] Patent Number: 5,347,078
[45] Date of Patent: Sep. 13, 1994

[54] SYRINGE NEEDLE DISPOSAL APPARATUS

[76] Inventor: John F. Eckels, 440 Jeremiah, #F, Simi Valley, Calif. 93065

[21] Appl. No.: 941,239

[22] Filed: Sep. 4, 1992

[51] Int. Cl.$^5$ .......................... A61M 5/32; B09B 1/00
[52] U.S. Cl. ................... 588/258; 588/250; 604/192; 206/365
[58] Field of Search ............ 604/110, 192; 206/365; 588/250, 258, 249

[56] References Cited

U.S. PATENT DOCUMENTS

| | | | |
|---|---|---|---|
| 3,226,007 | 12/1965 | Thies et al. | 206/365 |
| 4,610,667 | 9/1986 | Pedicano et al. | 604/192 |
| 4,623,336 | 11/1986 | Pedicano et al. | 604/192 |
| 4,735,311 | 4/1988 | Lowe et al. | 206/365 |
| 4,747,835 | 5/1988 | Sandhaus | 604/192 |
| 4,799,927 | 1/1989 | Davis et al. | 604/192 |
| 4,917,243 | 4/1990 | Abrams et al. | 206/365 |
| 4,950,242 | 8/1990 | Alvarez | 604/192 X |
| 4,973,315 | 11/1990 | Sincock | 206/192 |
| 4,986,817 | 1/1991 | Code | 604/192 |
| 5,046,612 | 9/1991 | Mostarda et al. | 206/365 |
| 5,084,027 | 1/1992 | Bernard | 604/192 |
| 5,085,647 | 2/1992 | Henderson et al. | 604/192 |
| 5,127,522 | 7/1992 | Ranford | 206/366 |
| 5,183,469 | 2/1993 | Capaccio | 206/365 X |
| 5,187,850 | 2/1993 | McCammon et al. | 604/110 X |
| 5,209,738 | 5/1993 | Bruno | 604/192 |

FOREIGN PATENT DOCUMENTS 2620942  3/1989  France ............ 604/192

*Primary Examiner*—Randolph A. Reese
*Assistant Examiner*—J. Russell McBee
*Attorney, Agent, or Firm*—William W. Haefliger

[57] ABSTRACT

Method and apparatus are provided for disposing of a hypodermic syringe needle and associated tip and hub, the syringe having a tubular body to which the hub is removably attached. The method includes providing an upright, protective receptacle having a downward entrance, and providing a trap door at the entrance; inserting the needle and hub into the receptacle via the entrance and past the trap door; and allowing the trap door to thus block withdrawal of the hub and needle from the receptacle in response to the insertion. The received needle and hub are contained in the receptacle for disposal; and penetrable sealant is also provided in the receptacle in a position to seal off the inserted needle tip from external contamination. Corresponding apparatus is also provided.

17 Claims, 4 Drawing Sheets

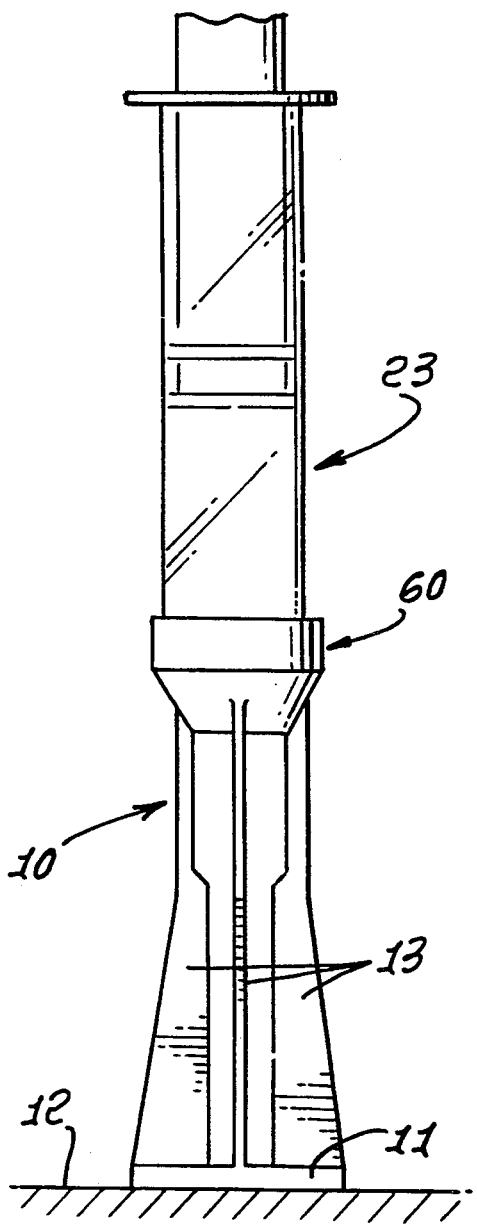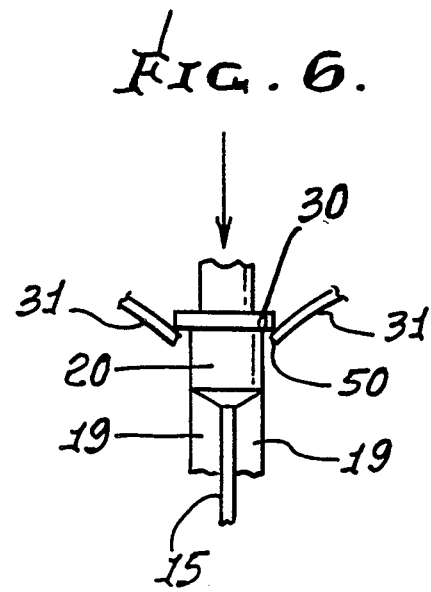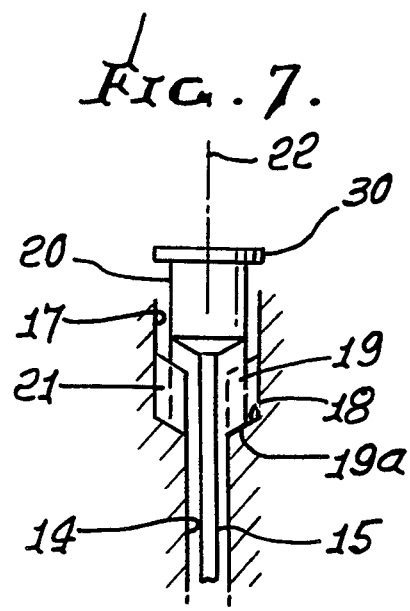

SYRINGE NEEDLE DISPOSAL APPARATUS

BACKGROUND OF THE INVENTION

This invention relates generally to safe disposal of hypodermic syringe needles, and more particularly to method and means for insertion, receiving and entrapping contaminated needles in containers so as to permit safe, easy separation of needle and syringe elements in the manner to be described.

There is continuing need for improved apparatus and method allowing rapid, easy and safe disposal of contaminated hypodermic syringe needles, as for example in hospitals. The danger of contamination of hospital staff during disposal of used needles is well known.

SUMMARY OF THE INVENTION

It is a major object of the invention to provide improved methods and means meeting the above need.

Objects of the invention include:

1) the provision of a free-standing needle disposal device into which a syringe needle may be easily inserted downwardly and forcibly;

2) provision of sealing, in the device, of an inserted needle end;

3) provision for entrapment of the contaminated needle in the containment device, once the needle is inserted;

4) provision of means to frictionally resist needle and needle hub rotation in the containment device, allowing easy, one-handed, rotary detachment and withdrawal of the syringe from the entrapped needle; and 5) provision for capping of the containment device after the detachment of the syringe from the entrapped needle; and 6) provision for easy viewing of the entrapped needle in the containment device.

The method of disposing of a hypodermic syringe needle, and associated hub, includes the steps:

a) providing an upright, protective receptacle having a downward entrance, and providing a trap door at the entrance, b) inserting the needle and hub into the receptacle via the entrance and past the trap door, c) and allowing the trap door to lbock withdrawal of the hub and needle from the receptacle in response to the insertion, d) whereby the received needle and hub are contained in the receptacle for disposal.

In regard to the above, the receptacle is typically supported in a free-standing, upright condition with the entrance presented upwardly, for downward reception of the needle and hub while attached to the syringe body, the body being separated later from the hub. The trap door may be provided with a deflectable lip to extend in interfering relation with the needle hub as the hub is inserted into the receptacle, and the lip is allowed to move into hub withdrawal blocking position in response to completed insertion of the hub into the receptacle.

A further object is to provide an insert sleeve inserted into the upper end of the receptacle, for connection to the receptacle, and providing the trap door and lip on that sleeve.

Yet another object is to provide ribbing in the receptacle to engage at least one of the needle and hub, to resist rotation thereof. The ribbing is located to prevent rotation of the hub and needle, while the syringe body is rotatably detached from the hub, as by unscrewing. Ribbing also resists endwise movement of the needle and hub, inserted into the receptacle, whereby the needle end does not "bottom out".

A further object is to provide means by which the inserted needle hub "bottoms out" as it is inserted, and at a location above the lower free end of the inserted needle, the latter received with sealant in the receptacle, during needle insertion.

These and other objects and advantages of the invention, as well as the details of an illustrative embodiment, will be more fully understood from the following specification and drawings, in which:

DRAWING DESCRIPTION

FIG. 1 is an external elevation showing apparatus incorporating the invention;

FIG. 6 is an elevation showing needle hub passage downwardly through entrapment means; and FIG. 7 is an elevation showing gripping of the needle hub to resist twist during removal of the syringe.

DETAILED DESCRIPTION

Figure 2:
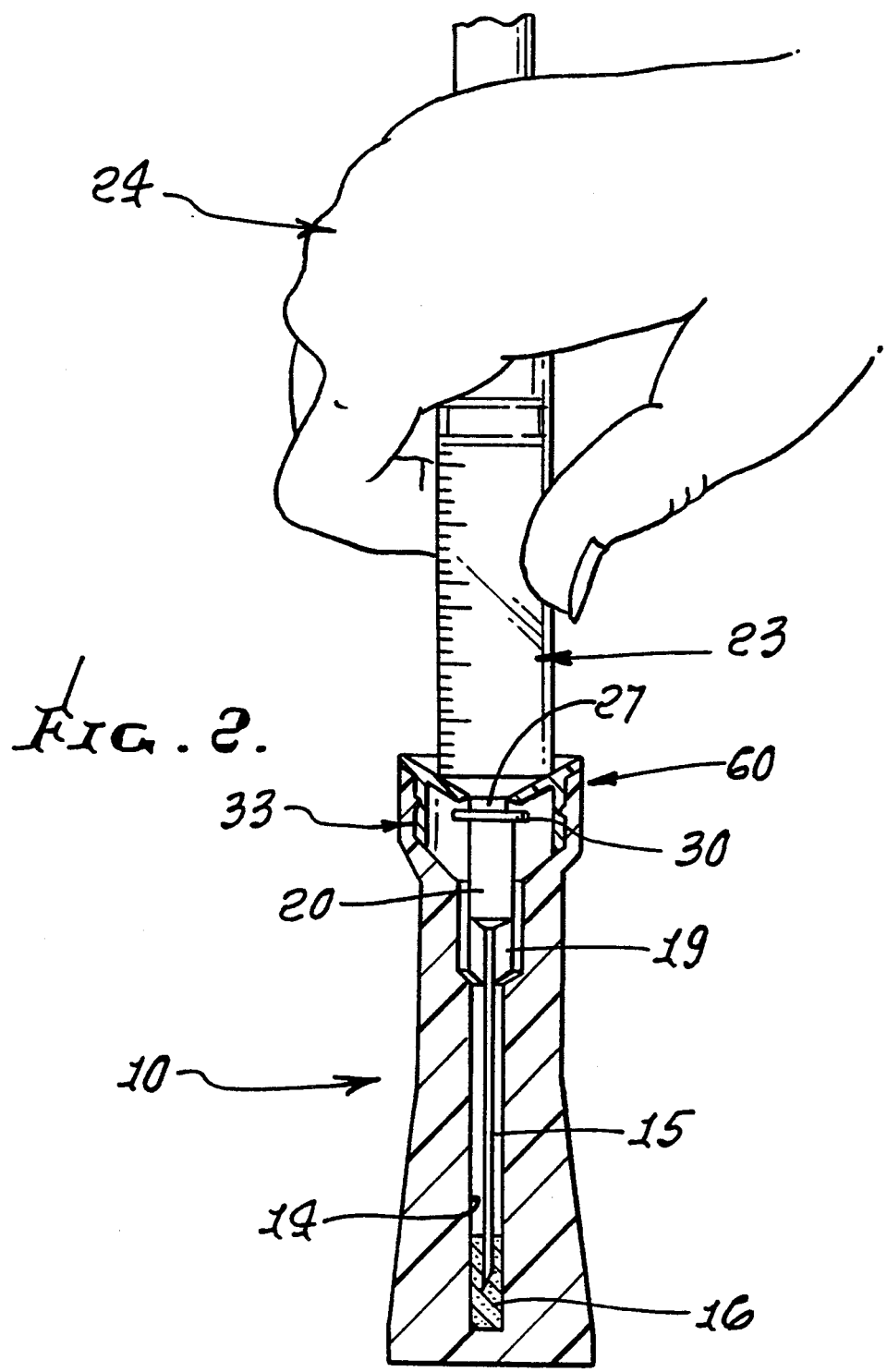
FIG. 2 is a section taken in elevation showing needle insertion into the apparatus receptacle.

In FIG. 1, an upright, protective receptacle 10 is provided to have an enlarged base 11 seated on a support surface 12. The receptacle has upright, stability fins 13 extending upwardly and inwardly from the base 11, about a tubular body 10a with which the fins are integral. The receptacle may, for example, consist of hard plastic material. Contained within the receptacle is a narrow, upright bore 14, to closely receive hypodermic needle 15. Sealant material 16, such as soft rubber or elastomer, or other material, is provided at the bottom of bore 14 to receive penetration of the needle tip 15a, for sealing off the tip and thereby preventing drainage of contaminating liquid from the needle into the bore. Also, the sealant blocks air entry into the needle that could contaminate the sample in the needle or syringe. Thus, the FIG. 2 configuration can be transported to other areas without external fluid contamination of fluid in the syringe. The needle lower tip does not engage the bottom of bore 14.

A counterbore 17 extends upwardly at a level above bore 14, and a downwardly tapering support shoulder 18 is formed between 17 and 14. Shoulder 18 is adapted to seat or "bottom" the lower edges 19a of ribs 19, integral with a needle hub 20, at the upper end of, and integral with, the needle 15, upon downward insertion or reception of the needle into the receptacle 10. See in FIG. 3 reception of the hub 20 into the upper end portion of the counterbore 17.

Associated with the receptacle are means, such as ribs 21, acting to resist rotation of the needle and its hub. See FIG. 7. Ribs 21 may project toward the vertical axis 22, in the counterbore 17, and between the circularly spaced ribs 19, to engage and block rotation of ribs 19 and the needle hub, as during rotary detachment of a syringe 23 from the needle hub.

Figure 3:
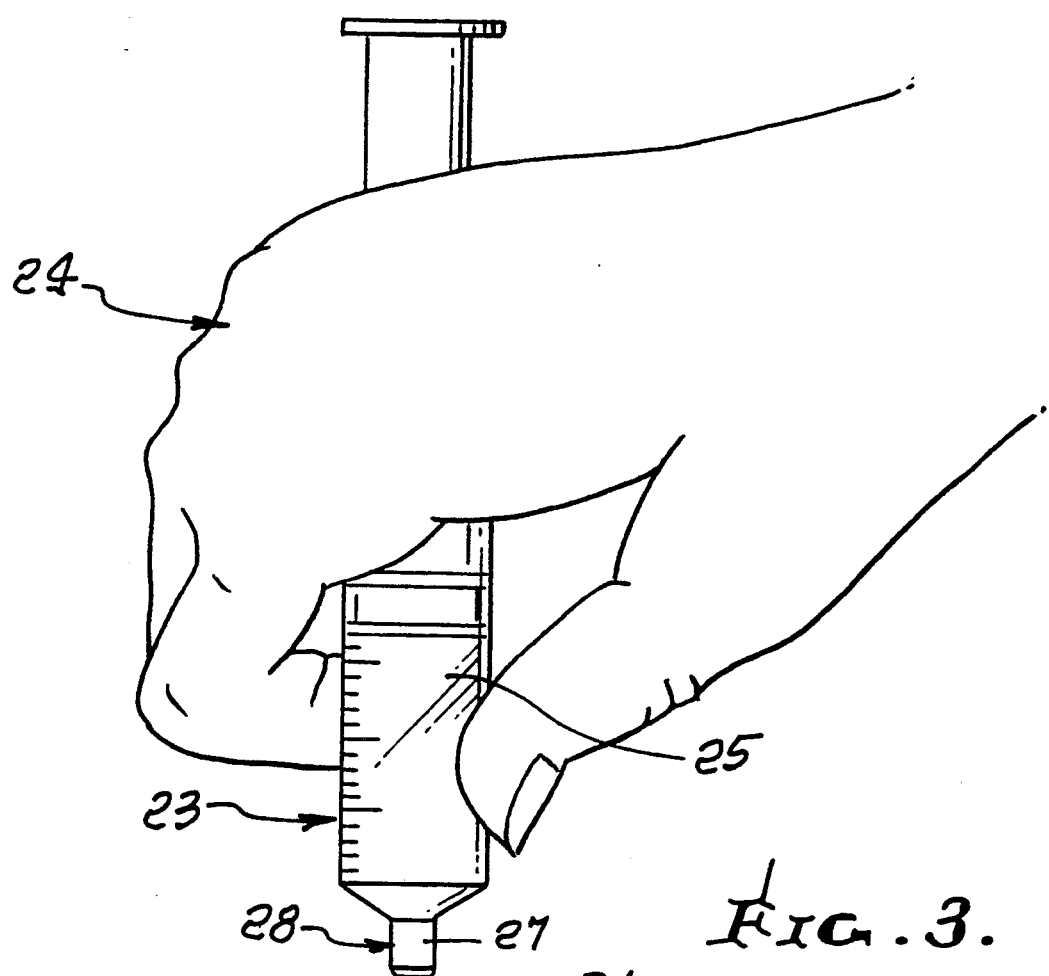
FIG. 3 is a view like FIG. 2 but showing detachment of the syringe from a needle hub, the needle locked in place.
Figure 4:
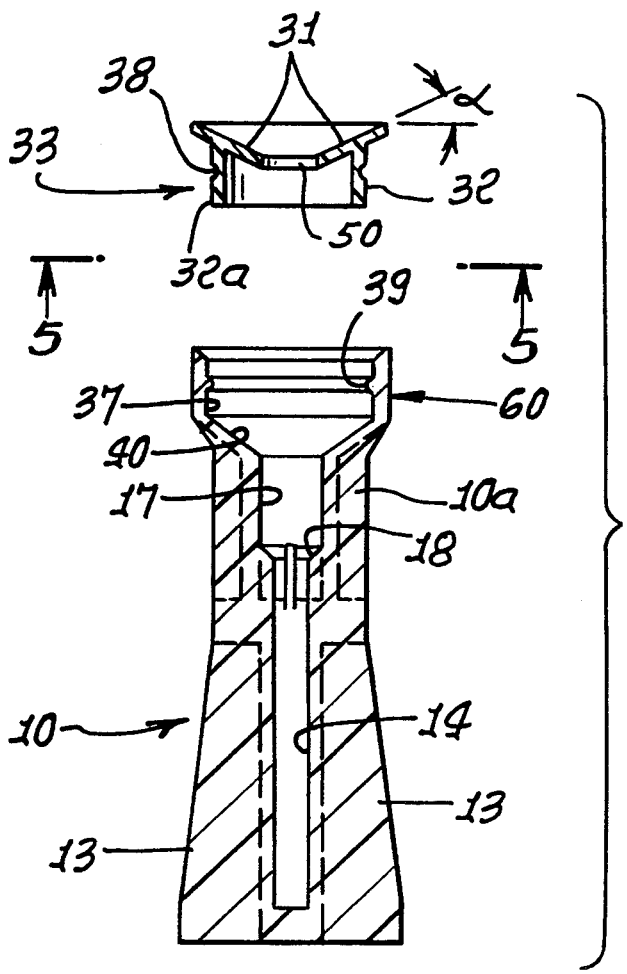
FIG. 4 is an elevation, taken in section, showing internal construction of the receptacle.

FIG. 3 shows the user's hand 24 gripping the syringe body 25, and, in a one-handed manner, rotating the syringe to detach it from the hub. Such detachment rotatably disconnects the external surface 27 on a syringe lower end tubular projection 28, from a corresponding internal surface 20a on the tubular hub 20, rotation of the hub and needle being resisted, as explained above. Surfaces 27 and 20a, when engaged, provide a frictional interfit.

In FIG. 1, the syringe is supported by the standing receptacle. The base 11 may be removably attached to surface 12, as by VELCRO (a trademark for hook-and-loop fasteners), or other attachment, whereby rotation of receptacle 10 is resisted.

Figure 5:
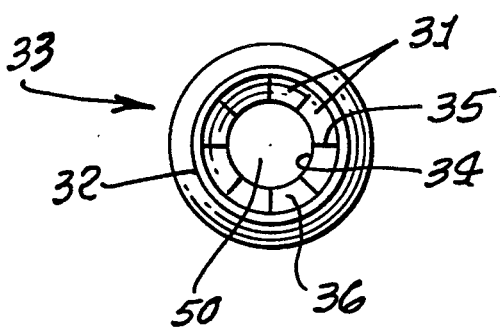
FIG. 5 is a plan view taken on lines 5—5 of FIG. 4.

Also provided is a withdrawal resisting means such as a trap door at the upper end of the receptacle, that door having a downward entrance 50 through which the needle 15, hub 20 and a flange 30 on the hub may pass, upon downward reception into the receptacle, while the hub is connected to the syringe. The trap door is shown in the form of flaps 31 having their outer extents integral with the tubular body 32 of an insert 33. The flaps project downwardly and inwardly, at a taper angle α, to terminate at a circular edge 34, defined by lips on the flaps seen in FIG. 5. That view shows the flaps formed by radial slits 35 in a frusto-conical cone 36, integral with body 32. The latter has downward sleeve extent 32a closely receivable into a second counterbore 37 in a head 60, on and integral with the receptacle. Detenting at 38 and 39 holds the sleeve in axially received position in the receptacle, as seen in FIG. 3.

Figure 5A:
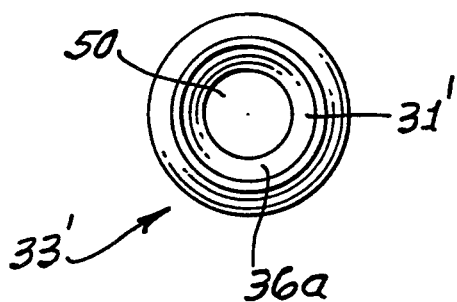
FIG. 5a is a plan view like FIG. 5 showing a modification.

FIG. 5a shows a frusto-conical wall 36a, without slits.

FIG. 6 shows the needle hub flange 30 passing downwardly through entrance 50, deflecting flaps 31 downwardly. After the flange passes below the inner edges of the flaps, they resiliently and yieldably return to FIG. 3 position, locking the hub and its flange in position in the receptacle bore and counterbore. Also, the syringe lower tip portion 28 may then be rotatably disconnected from the hub. Note that the diameter of the flange 30 is greater than the diameter of the circular edge 34 defined by the flaps in undeflected state.

The fit of the circular hub 20 or ribs 19 in the counterbore 17 may be an interference fit to center the hub in the receptacle, coaxially with axis 22. Note downward sloping shoulder 40 between counterbore 17 and counterbore 37, acting to guide and center the downward tapering lower edges at 19a of ribs 19, as the needle is inserted in the receptacle.

Accordingly, the invention provides for safe syringe separation from the needle, and enclosed and unexposed storage of the needle in firmly centered position. The walls of the receptacle 10 may be transparent for ease of viewing of the needle and its position.

Blood is typically filled into the syringe tubular body, via the needle, prior to disposal of the needle, as described.

After the needle is captivated in the receptacle, a cap 70 is fitted over head 60, as seen in FIG. 3, to seal off the top of the receptacle, for complete isolated containment of the contaminated needle.

FIG. 5a shows a modified sleeve 33', with a single conical flap 31', with no slits. The sleeve 33' is otherwise like 33.

I claim:

1. The method of disposing of the needle of a hypodermic syringe, the needle having an associated tip and hub, the syringe also having a tubular body to which the hub is removably attached, that includes:
    a) providing an upright, protective receptacle having a downward entrance, and providing a trap door at said entrance,
    b) inserting the needle and hub into the receptacle via said entrance and past said trap door,
    c) and allowing said trap door to block withdrawal of the hub and needle from the receptacle in response to said insertion,
    d) whereby the received needle and hub are contained in the receptacle for disposal,
    e) providing penetrable sealant in the receptacle in a position to seal off the contained needle tip from external contamination,
    f) providing ribbing means in said receptacle to engage at least one of the needle and hub, to resist rotation thereof,
    g) and detaching said tubular body from said hub while the hub is located in the receptacle.

2. The method of claim 1 including supporting the receptacle in a free standing upright condition with said entrance presented upwardly, for downward reception of the needle and hub while attached to the syringe body, and subsequently separating said body from the hub.

3. The method of claim 1 including filling blood into the syringe tubular body, via the needle, prior to said insertion step.

4. The method of claim 1 wherein the trap door defines an opening, and wherein the needle and hub are passed through said trap door opening into the receptacle.

5. The method of claim 4 including providing said trap door with a deflectable lip to extend in interfering relation with the needle hub as the hub is inserted into the receptacle, and allowing said lip to move into hub withdrawal blocking position in response to completed insertion of the hub into the receptacle.

6. The method of claim 5 including providing an insert sleeve, and inserting said sleeve into said receptacle at the top of thereof, for connection to the receptacle, said trap door and lip integral with the sleeve.

7. The method of disposing of the needle of a hypodermic syringe, the needle having an associated tip and hub, the syringe also having a tubular body to which the hub is removably attached, that includes:
    a) providing an upright, protective receptacle having a downward entrance, and providing a trap door at said entrance,
    b) inserting the needle and hub into the receptacle via said entrance and past said trap door,
    c) and allowing said trap door to block withdrawal of the hub and needle from the receptacle in response to said insertion,
    d) whereby the received needle and hub are contained in the receptacle for disposal,
    e) providing penetrable sealant in the receptacle in a position to seal off the contained needle tip from external contamination,
    f) and providing ribbing in said receptacle to engage at least one of the needle and hub, to resist rotation thereof.

8. The method of claim 1 wherein said detaching is effected by rotation of said body relative to said hub.

9. The method of claim 7 including detaching said tubular body from said hub while the hub is located in the receptacle.

10. The method of claim 9 wherein said detaching is effected by rotation of said body relative to said hub, and while said ribbing prevents rotation of the needle and hub.

11. The method of claim 1 including providing a cap and applying the cap to the receptacle to extend across laid entrance, for sealing said entrance.

12. The method of disposing of the needle of a hypodermic syringe, the needle having an associated tip and hub, the syringe also having a tubular body to which the hub is removably attached, that includes:
   a) providing an upright, protective receptacle having a downward entrance, and providing a trap door at said entrance,
   b) inserting the needle and hub into the receptacle via said entrance and past said trap door,
   c) and allowing said trap door to block withdrawal of the hub and needle from the receptacle in response to said insertion,
   d) whereby the received needle and hub are contained in the receptacle for disposal,
   e) providing penetrable sealant in the receptacle in a position to seal off the contained needle tip from external contamination,
   f) supporting the receptacle in a free standing upright condition with said entrance presented upwardly, for downward reception of the needle and hub while attached to the syringe body, and subsequently separating said body from the hub,
   g) and providing a bore in the receptacle with said sealant therein to receive penetration of the needle, and providing a counterbore in the receptacle within which said hub is received, for locating the hub and needle in the receptacle.

13. Apparatus for disposing of the needle of a hypodermic syringe, the needle having an associated hub, the syringe also having a tubular body to which the hub is removably attached, that includes:
   a) an upright, protective receptacle having a downward entrance, and a trap door at said entrance,
   b) the needle and hub to be inserted into the receptacle via said entrance and past said trap door,
   c) the trap door configured to block withdrawal of the hub and needle from the receptacle in response to said insertion,
   d) whereby the received needle and hub are contained in the carrier for disposal,
   e) a bore in the receptacle with sealant therein to receive penetration of the needle, with the receptacle supported in standing position and a counterbore in the receptacle within which said hub is received, for locating the hub and needle in the receptacle.

14. The apparatus of claim 13 including a support base on the receptacle to support the receptacle, inserted and sealed needle, and syringe, in upright positions.

15. The method of disposing of the needle of a hypodermic syringe, the needle having an associated tip and hub, the syringe also having a tubular body to which the hub is removably attached, that includes:
   a) providing an upright, protective receptacle having a downward entrance, and providing a withdrawal resistance means proximate said entrance,
   b) inserting the needle and hub into the receptacle via said entrance and past said means,
   c) and allowing said means to resist withdrawal of at least one of the hub and needle from the receptacle in response to said insertion,
   d) whereby the received needle and hub are contained in the receptacle for disposal,
   e) providing penetrable sealant in the receptacle in a position to seal off the contained needle tip from external contamination,
   f) and providing ribbing in said receptacle to engage at least one of the needle and hub, to resist rotation thereof.

16. The method of claim 15 including locating said withdrawal resistance means to engage the hub, during said inserting step.

17. Apparatus for disposing of the needle of a hypodermic syringe, the needle having an associated hub, the syringe also having a tubular body to which the hub is removably attached, that includes:
   a) an upright, protective receptacle having a downward entrance, and withdrawal resisting means proximate said entrance,
   b) the needle and hub to be inserted into the receptacle via said entrance and past said withdrawal resisting means,
   c) the withdrawal resisting means configured to block withdrawal of at least one of the hub and needle from the receptacle in response to said insertion,
   d) whereby the received needle and hub are contained in the receptacle carrier for disposal, and
   e) a bore in the receptacle with sealant therein to receive downward penetration of the needle, with the receptacle supported in standing position and structure in the receptacle within which said hub is received, for locating the hub and needle in the receptacle, and
   f) ribbing in said receptacle to engage at least one of the needle and hub, to resist rotation thereof.

* * * * *